United States Statutory Invention Registration [19]

[11] Reg. Number: H852

Garden et al. [43] Published: Nov. 6, 1990

[54] RODENTICIDAL COMPOSITION

[75] Inventors: Alan R. Garden, Rochester; Malcolm R. Hadler, Cheshire, both of England

[73] Assignee: E. I. Du Pont de Nemours and Company, Inc., Wilmington, Del.

[21] Appl. No.: 265,296

[22] Filed: Oct. 27, 1988

[30] Foreign Application Priority Data

Dec. 18, 1987 [GB] United Kingdom ..... 8729557

[51] Int. Cl.[5] ..... A01N 43/18; C07D 335/06

[52] U.S. Cl. ..... 514/432; 514/457; 514/456; 514/681; 549/23; 549/286; 568/327

[58] Field of Search ..... 549/285, 204, 286; 514/457

[56] References Cited

U.S. PATENT DOCUMENTS

| | | | |
|---|---|---|---|
| 2,297,212 | 9/1942 | Gockel | 549/204 |
| 2,310,949 | 2/1943 | Ford et al. | 167/24 |
| 2,427,578 | 9/1947 | Stahmann et al. | 260/333 |
| 2,648,682 | 8/1953 | Stoll et al. | 260/343.2 |
| 2,672,483 | 3/1954 | Thomas | 260/590 |
| 2,952,689 | 9/1960 | Enders et al. | 260/343.2 |
| 3,153,612 | 10/1964 | Molho et al. | 167/46 |
| 3,574,234 | 4/1971 | Boschetti et al. | 260/332.2 |
| 3,651,091 | 3/1972 | Boschetti et al. | 260/343.2 |
| 3,651,233 | 3/1972 | Boschetti et al. | 424/275 |
| 3,764,693 | 10/1973 | Boschetti et al. | 424/281 |
| 3,787,585 | 1/1974 | Ueno et al. | 549/204 |
| 3,957,824 | 5/1976 | Hadler et al. | 260/343.2 R |
| 4,520,007 | 5/1985 | Entwistle et al. | 424/17 |
| 4,585,786 | 4/1986 | Berthelon | 514/432 |

FOREIGN PATENT DOCUMENTS 2126578 3/1984 United Kingdom .

*Primary Examiner*—John S. Maples
*Assistant Examiner*—Joseph D. Anthony

[57] ABSTRACT

A method for stabilizing a rodenticidally active material selected from certain (i) indane dione derivatives, (ii) hydroxycoumarin derivatives and (iii) thiocoumarin analogs of (ii), comprising bringing said active material into contact with, and maintaining the active material in contact with, an acidic stabilizer.

3 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

RODENTICIDAL COMPOSITION

The present invention relates to rodenticidal compositions, to a method of stabilising a rodenticidally active material, and to a method of exterminating rodents.

Anticoagulant rodenticidal compositions are known which comprise indane dione derivatives as active ingredient. Commercial rodenticides include pindone, diphacinone and chlorophacinone. These compounds have the general formula I

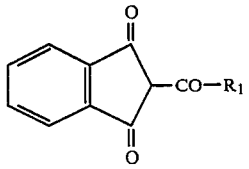

I in which $R_1$ can be a tertiary butyl group, yielding pindone (see U.S. Pat. No. 2,310,949), an alpha-phenyl benzyl group, yielding diphacinone (see U.S. Pat. No. 2,672,483) or an alpha-(4-chlorophenyl)benzyl group, yielding chlorophacinone (see U.S. Pat. No. 3,153,612).

Over the years a number of coumarin-derivatives with anti-coagulant properties have been developed which are useful as rodenticides. The coumarin derivative can be described as a compound of formula II

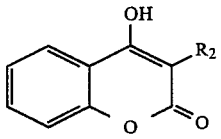

II in which $R_2$ can have several meanings

From U.S. Pat. No. 2,427,578 compounds are known in which $R_2$ can be a grouping

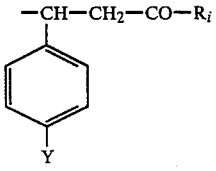

in which $R_i$ represents a $C_{1-6}$ alkyl group and Y is a hydrogen atom. The compound in which $R_i$ is a methyl group is known as warfarin. The compound coumachlor, in which $R_i$ is methyl group and Y is a chlorine atom, is described in U.S. Pat. No. 2,648,682.

Compounds in which $R_2$ is a group

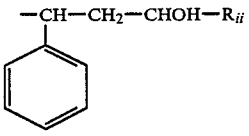

in which $R_{ii}$ represents a diphenyl group optionally substituted with one or more halogen atoms are known from DE-A-No. 1,959,317. The compound in which $R_{ii}$ is 4'-bromo-diphenyl is known as bromadiolone.

Further, compounds are known in which $R_2$ represents a group

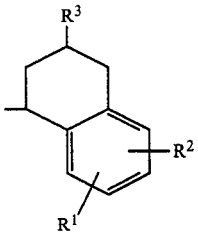

When $R^1=R^2=R^3=H$ the compound is known as coumatetralyl as described in U.S. Pat. No. 2,952,689.

U.S. Pat. No. 3,957,824 discloses a class of compounds in which $R_2$ has the above meaning and in which $R^1$ and $R^2$ are the same or different and are hydrogen or halogen atom, preferably chlorine or bromine, or alkyl or alkoxy groups, preferably having up to 6 carbon atoms, $R^3$ is an aryl group having the formula

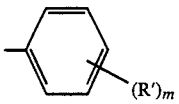

where m is 1 or 2, and R' is the same or different and is a halogen atom, a straight or branched chain alkyl or alkoxy group, preferably containing at least 2, more preferably from 5 to 12 carbon atoms, a cycloalkyl, preferably cyclohexyl group, an aralkyl, preferably alpha-aralkyl group, a phenyl or a phenoxy group , or a halogeno, preferably para halogeno, substituted derivative thereof. The halogen atom or atoms are preferably chlorine or bromine. Where m is 1, R' is preferably in the para position and when m is 2 one of the R' groups is preferably in the para position. Preferably $R^3$ contains at least 1 but not more than 3 and optimally not more than 2 halogen atoms.

Two specific compounds are that wherein $R^1$ and $R^2$ are both hydrogen and $R^3$ is a 4-phenylphenyl group (difenacoum) and that wherein $R^1$ and $R^2$ are both hydrogen and $R^3$ is a 4-(4-bromophenyl)phenyl group (brodifacoum).

GB-A-No. 2 126 578, and the corresponding EP-A-No. 98 629, discloses a further class of 4-hydroxycoumarin derivatives having anticoagulant properties, particularly as rodenticides. In their broadest definition, these compounds have the formula

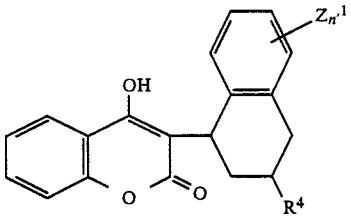

in which $Z^1$ represents a halogen atom, preferably a chlorine atom, and n' is 0, 1 or 2 and $R^4$ represents either (1) a grouping which comprises a phenylene radical attached directly or indirectly to the tetralin ring and having in the para position (with respect to such attachment) an electron-withdrawing atom or group whose rotational volume substantially does not exceed that of a phenyl group and which forms together with said phenylene radical a polarisable structure, or (2) a grouping selected from

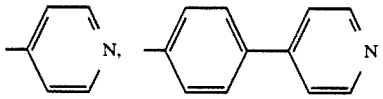

and

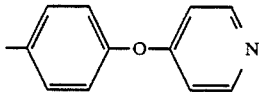

or (3) a grouping which comprises a phenylene radical attached directly to the tetralin ring and having in the para position (with respect to such attachment) a substituted furanyl or thiophenyl radical attached thereto directly or through oxygen and/or methylene, said furanyl or thiophenyl radical having an electron-withdrawing atom or group as a substituent in a position forming with the furanyl or thiophenyl radical a polarisable structure, said atom or group having a rotational volume which substantially does not exceed that of a phenyl group.

In the above formula, $R^4$ is preferably more specifically defined as a group

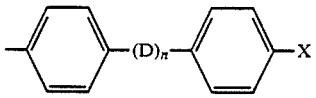

where X is a hydrogen or halogen atom or a group CN or $CF_3$, n is 0 or 1 and D is an oxygen atom or a group —O—$CH_2$—, —$CH_2$—$CH_1$—, —$CH_2$—$CH_2$—$CH_2$— or —CH=CH—.

In EP-A-No. 161,163 thioanalogues of hydroxy coumarin rodenticides are described which analogues have the general formula III

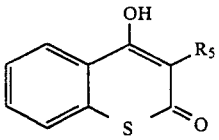

III in which $R_5$ can be selected from a tetrahydronaphthyl group of formula

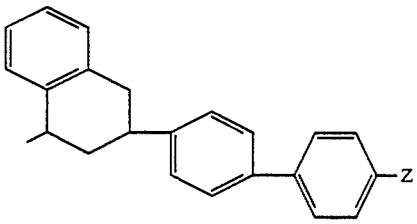

or a grouping of formula

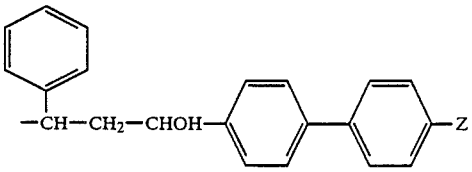

in which Z is a hydrogen or halogen atom.

As indicated above the compounds have anti-coagulant properties which render them suitable for use as rodenticides. Thereto, the rodenticidally active compounds are mixed with one or more carriers to form a bait. This applies to any of the stereoisomers of the above rodenticidally active compounds.

The rodenticidally active compounds, described above, are in general stable and do not decompose. However, it has been found that when these compounds were used in certain baits and when after a while the amount of rodenticidally active material was determined, the results indicated that not all active material could be recovered, which would appear to indicate that decomposition has taken place. This phenomenon was especially observed at the so-called loose grain baits, i.e. baits whereby the active material together with carrier(s) has been applied onto grain particles. These particles include both whole grains and grain pieces. Research showed that most likely the active material does not decompose but is strongly bound to the grain matrix.

In order to be able to easily check the concentration of rodenticidally active matter in such baits, it would be advantageous if rodenticidal compositions were used of which the active ingredient would not be bound to the grain matrix. It has now been found that the inclusion of certain acidic stabilisers improves the composition by substantially preventing the binding of rodenticidally active material to the grain matrix.

Accordingly, the present invention provides a rodenticidal composition comprising a rodenticidally active material selected from (i) an indane dione derivative of formula I

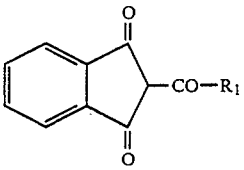

I in which $R_1$ is a tertiary butyl group or an alphaphenylbenzyl group or an alpha-(4-chlorophenyl)benzyl group;

(ii) a hydroxy coumarin derivative of formula II

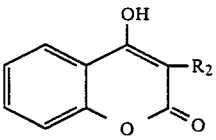

II in which $R_2$ is selected from groupings having formulae

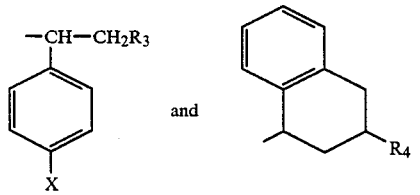

in which X is a hydrogen or a halogen atom, $R_3$ is a 1-biphenyl-1-hydroxy-methyl group optionally substituted at the 4'-position by a halogen atom, or a methylcarbonyl group, and $R_4$ is hydrogen or a group of formula

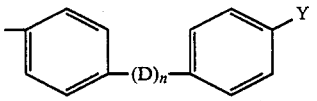

in which n is 0 or 1, D is an oxygen atom or a $—OCH_2—$, $—CH_2—CH_2—$, $—CH_2—CH_2—CH_2—$ or —HC=CH— group and Y is a hydrogen atom, a halogen atom or a CF3 or CN group; and (iii) a thiocoumarin analogue of formula III

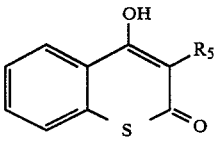

III in which $R_5$ is a tetrahydronaphthyl group of formula

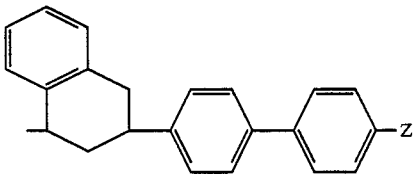

or a grouping of formula

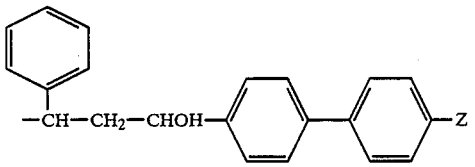

in which Z is a hydrogen or halogen atom; in combination with acidic stabiliser selected from the group consisting of (1) a compound of formula IV $R_6—COOH$ (IV)

in which $R_6$ is a hydrocarbyl group having 1 to 12 carbon atoms in which group one or more non-terminal carbon atoms are optionally replaced by one or more nitrogen, oxygen or sulphur atoms, and which group is optionally substituted by one or more hydroxy, oxo or carboxyl groups;

(2) a five- or six-membered ring compound which contains in the ring an enediol grouping of formula

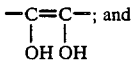

(3) an acid selected from phosphoric, sulphuric, hydrochloric, methylsulphonic and arylsulphonic acids.

The rodenticidal composition according to the present invention is of particular interest when it comprises difenacoum, brodifacoum or flocoumafen, i.e. (3-[3-(4-(4-trifluoromethylbenzyloxy)phenyl)-1,2,3,4-tetrahydro-1-naphthyl]-4-hydroxycoumarin. This means that $R_4$ is a diphenyl or 4'-bromo-diphenyl group or a group

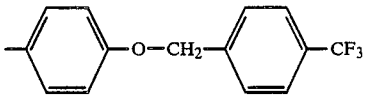

Any of these three compounds can be used in the cis or trans or mixed cis/trans form.

The preparation of the rodenticidally active compounds is described in the above respective patent documents. An advantageous method of preparing those coumarin compounds of formula II in which $R_2$ is a substituted tetrahydronaphthyl group is described in EP-A-No. 177,080.

In the acidic stabiliser of formula IV $R_6$ has preferably 1 to 8 carbon atoms, of which up to three may be replaced by a heteroatom. Since compounds having a hydroxyl group and/or an oxo and/or a further carboxyl group appear to be more effective, $R_6$ is preferably substituted by one or more hydroxy, oxo and/or additional carboxyl groups. Suitable acids include aliphatic acids, such as acetic, propionic, butyric, malonic, maleic, succinic, pentanoic, hexanoic, heptanoic, octanoic acid, all of which can be substituted by one or more hydroxyl groups, and aromatic acids, such as benzoic, toluic, salicylic, anisic and (tere)phthalic acid, and also heteroaromatic acids such as picolinic, nicotinic and isonicotinic acid. When the acids are available in stereoisomeric forms, all pure forms and the racemic mixtures can be used. When one or more of the non-terminal carbon atoms of $R_6$ is replaced by a heteroatom, the heteroatom is preferably a nitrogen atom. Suitable examples of such acidic stabilisers include nitrilotriacetic acid and ethylene diamino tetraacetic acid.

When the acid stabiliser is selected from five- and six-membered ring compounds having an enediol group the compound has preferably one or more further hydroxyl substituents and/or a hetero atom, selected from O, S and N in the ring. Suitable compounds include polyhydroxybenzenes, having at least hydroxyl groups on two adjacent carbon atoms and substituted polyhydroxy-benzenes. Most preferred is ascorbic acid, either in a racemic mixture or in pure stereoisomeric form.

Suitable arylsulphonic acids which can be used in the present invention include benzene, toluene and xylene sulphonic acids. Preferred is p-toluene sulphonic acid.

Amongst all acids comprised under (3) phosphoric acid is the most preferred.

However, preferably the acidic stabiliser is selected from benzoic, succinic, citric, lactic, propionic, tartaric, ethylene diamino tetraacetic and ascorbic acid; most preferred is citric acid.

The quantity of the acidic stabiliser can be varied within wide limits. One of the things which are relevant to the acid quantity is the palatability of the composition to rodents. Preferably, the weight ratio of acidic stabiliser to the rodenticidally active material ranges from 25:1 to 500:1, more preferably from 50:1 to 250:1 in case acidic stabilisers from groups (1) and (2) are used. When the strong acids of group (3) are employed, the weight ratio of acidic stabiliser to the rodenticidally active material is advantageously from 1:1 to 100:1.

The invention also provides a method of stabilising a rodenticidally active material as defined above which comprises bringing said active material into admixture with an acidic stabiliser as defined above. This invention, because it provides for admixing the active material and acidic stabilizer, will be understood by those skilled in the art to effect a continuous stabilization process by the very fact of maintaining the active material and acidic stabilizer in admixture. While the acidic stabilizer is contacting the active material, and for so long as the contact is maintained, the stability of the active material is being assured.

Further in accordance with the invention there is provided a method of exterminating rodents which comprises providing at a locus a composition according to the invention.

Compositions according to the invention may contain up to 50% w active ingredient, e.g. from 0.0005 to 50% w of the rodenticidal coumarin derivative. They may be in the form of a bait concentrate, which in use may be diluted by mixing with appropriate quantities of bait base. Accordingly, the rodenticidal composition as described above may further contain a bait base. The bait base preferably consists of loose grain, grain particles or ground grain. The bait base can be selected from e.g. wheat, barley, oats, rye, maize, rice, millet or sorghum. The composition may further contain flavouring agents, such as salt, sodium glutamate, sugar or saccharin. Usually a warning dye will be included for safety reasons. Other additives which may be present in rodenticidal compositions include surfactants, oils, waxes, thickeners, gums, chopped or mixed fruit or vegetables.

The invention will be further understood from the following example.

EXAMPLE

A bait base containing 0.5% w flocoumafen, 2.5% w blue dyestuff, and the balance carrier/flavouring agents was mixed with one half, one or two parts by weight of acid stabiliser and the obtained mixture was applied onto wheat grain using 1½ parts by weight of a mineral oil ("ONDINA 68" (trade mark) refined white mineral oil).

The amount of flocoumafen was determined by the following procedure. The grains were ground and subjected to extraction with acetonitrile containing 0.2% vol. of a mixture of acetic acid and water (volume ratio 40:60). The amount of flocoumafen was determined by high performance liquid chromatography (HPLC) together with ultraviolet detection at 220 nm, using external calibration, the mobile phase being the same as the extraction fluid.

The samples were stored at 54° C. for 2 weeks to simulate about a 2 year ageing period at ambient temperature. The amount of recoverable active matter was determined as described above. The results of the tests are indicated in the following Table.

| Exp. No. | Flocoumafen amount mg/kg | Acid Stabilizer name | Acid Stabilizer amount g/kg | Recovered flocoumafen mg/kg | % unrecovered |
|---|---|---|---|---|---|
| 1 | 49 | benzoic acid | 5 | 39 | 20 |
| 2 | 51 | propionic acid | 5 | 41 | 20 |
| 3 | 48 | succinic acid | 5 | 39 | 19 |
| 4 | 48 | lactic acid | 5 | 42 | 13 |
| 5 | 48 | citric acid | 10 | 46 | 4 |
| 6 | 50 | citric acid | 5 | 45 | 10 |
| 7 | 48 | citric acid | 2.5 | 40 | 17 |
| 8 | 47 | ascorbic acid | 5 | 41 | 13 |
| 9 | 49 | EDTA | 5 | 40 | 18 |
| 10 | 55 | tartaric acid | 5 | 46 | 16 |
| 11 | 51 | oleic acid | 5 | 36 | 29 |
| 12 | 42 | — | — | 31 | 26 |

From the above results, in which Experiments 1 to 10 are in accordance with the invention, Experiments 11 and 2 being comparative experiments, it is apparent that the effectiveness of the acid stabiliser is improved when the compound contains an additional carboxyl group (cf. exp. 2 and 3) or a hydroxyl group (cf. exp. 2 and 4). The best results are obtained with acids containing both additional carboxyl and hydroxyl groups, viz. citric acid.

The comparative Experiment 11 shows that acid of formula $R_6$—COOH in which $R_6$ is a hydrocarbyl group with 17 car atoms does not perform well and the results of experiment 11 are even worse than those of the comparative experiment 12 in which no acidic stabiliser was used.

We claim:

1. A method for stabilizing a rodenticidally active material selected from:

a hydroxycoumarin derivative of formula II

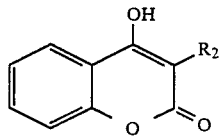

II in which $R_2$ is selected from groupings having formulae

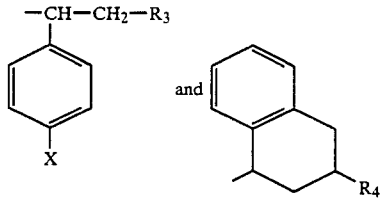

in which X is a hydrogen or a halogen atom, $R_3$ is a 1-biphenyl-1-hydroxy-methyl group optionally substituted at the 4'-position by a halogen atom, or a methylcarbonyl group, and $R_4$ is hydrogen or a group of formula

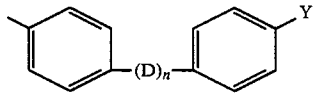

in which n is 0 or 1, D is an oxygen atom or a $—OCH_2—$, $—CH_2—CH_2—$, $—CH_2—CH_2—CH_2—$ or —HC=CH— group and Y is a hydrogen atom, a halogen atom or a $CF_3$ or CN group;

comprising bringing said active material into admixture with an acidic stabilizer selected from the group consisting of lactic acid, ascorbic acid, citric acid, succinic acid, ethylenediamine tetraacetic acid, and tartaric acid.

2. A method according to claim 1 wherein the hydroxycoumarin derivative is flocoumafen and the acidic stabilizer is citric acid.

3. A method according to claim 1 or 2 comprising maintaining the active material and acidic stabilizer in continuous admixture thereby effecting continuous stabilization of the active material.

* * * * *